United States Patent
Horiuchi et al.

(10) Patent No.: US 10,684,222 B2
(45) Date of Patent: Jun. 16, 2020

(54) POWDER DUSTINESS EVALUATION METHOD AND POWDER DUSTINESS EVALUATION DEVICE

(71) Applicant: YOSHINO GYPSUM CO., LTD., Tokyo (JP)

(72) Inventors: Tatsuya Horiuchi, Tokyo (JP); Kenichi Sugano, Tokyo (JP)

(73) Assignee: YOSHINO GYPSUM CO., LTD., Tokyo (JP)

( * ) Notice: Subject to any disclaimer, the term of this patent is extended or adjusted under 35 U.S.C. 154(b) by 36 days.

(21) Appl. No.: 16/082,620

(22) PCT Filed: Apr. 14, 2017

(86) PCT No.: PCT/JP2017/015308
§ 371 (c)(1),
(2) Date: Sep. 6, 2018

(87) PCT Pub. No.: WO2017/191745
PCT Pub. Date: Nov. 9, 2017

(65) Prior Publication Data
US 2019/0025206 A1    Jan. 24, 2019

(30) Foreign Application Priority Data
May 2, 2016 (JP) .................................. 2016-092290

(51) Int. Cl.
*G01N 21/51* (2006.01)
*G01N 21/47* (2006.01)
(Continued)

(52) U.S. Cl.
CPC ............. *G01N 21/51* (2013.01); *G01N 15/06* (2013.01); *G01N 2015/0046* (2013.01);
(Continued)

(58) Field of Classification Search
CPC ........... G01N 21/51; G01N 2015/0096; G01N 2015/0046; G01N 2021/4769; G01N 15/06; G01N 2033/0091
See application file for complete search history.

(56) References Cited

U.S. PATENT DOCUMENTS 4,775,991 A * 10/1988 Staudinger ............. G01N 15/04
378/51
4,830,194 A * 5/1989 Kajiura ................. B07C 5/3425
209/580
(Continued)

FOREIGN PATENT DOCUMENTS

CN     105547930      5/2016
JP     62-212255      9/1987
(Continued)

OTHER PUBLICATIONS

International Search Report, issued in the corresponding PCT application No. PCT/JP2017/015308, dated Jul. 4, 2017, 3 pages.
(Continued)

Primary Examiner — Sang H Nguyen
(74) Attorney, Agent, or Firm — Hamre, Schumann, Mueller & Larson, P.C.

(57) ABSTRACT

The present invention intends to provide a method by which the scattering property of a powder can be more clearly evaluated. There is provided a method for evaluating a scattering property of a powder, the method including dropping a powder to be evaluated onto a liquid placed in a box, thereby scattering the powder as dust in the box, and measuring a dust concentration in air in the box with a dust meter. There is also provided an apparatus for evaluating a scattering property of a powder, the apparatus including a box in which a liquid is to be placed, and a dust meter that measures a dust concentration in air in the box when the (Continued)

powder to be evaluated drops onto the liquid placed in the box and scatters as dust.

16 Claims, 4 Drawing Sheets

(51) Int. Cl.
    *G01N 15/06*     (2006.01)
    *G01N 15/00*     (2006.01)
    *G01N 33/00*     (2006.01)

(52) U.S. Cl.
    CPC ............ *G01N 2015/0096* (2013.01); *G01N 2021/4769* (2013.01); *G01N 2033/0091* (2013.01)

(56) References Cited

U.S. PATENT DOCUMENTS

| | | | | |
|---|---|---|---|---|
| 4,976,540 A * | 12/1990 | Kitamura | ............ | G01N 21/85 356/237.3 |
| 5,242,059 A * | 9/1993 | Low | ............ | B07C 5/362 198/370.12 |
| 5,561,515 A * | 10/1996 | Hairston | ............ | G01P 5/22 356/28 |
| 5,701,012 A * | 12/1997 | Ho | ............ | G01N 15/1459 250/461.2 |
| 5,818,577 A * | 10/1998 | Duclos | ............ | B07C 5/3427 356/237.1 |
| 6,352,585 B1 * | 3/2002 | Diesso | ............ | C04B 24/04 106/35 |
| 2003/0150928 A1 * | 8/2003 | Watanabe | ............ | A61J 3/10 239/1 |
| 2007/0157990 A1 * | 7/2007 | Amano | ............ | B65B 1/16 141/83 |
| 2007/0176783 A1 * | 8/2007 | Knox | ............ | G08B 17/10 340/607 |
| 2008/0148869 A1 * | 6/2008 | Otani | ............ | G01N 15/06 73/863.21 |
| 2010/0201983 A1 * | 8/2010 | Hatano | ............ | G01M 3/38 356/337 |
| 2010/0304010 A1 * | 12/2010 | Powell | ............ | G01F 1/30 427/8 |
| 2011/0140012 A1 | 6/2011 | Cranfill, III et al. | | |
| 2014/0092386 A1 * | 4/2014 | Wei | ............ | G01N 15/1425 356/338 |
| 2015/0377764 A1 * | 12/2015 | Pan | ............ | G01N 15/1434 356/36 |
| 2016/0327883 A1 * | 11/2016 | Nakamoto | ............ | G03G 9/09733 |

FOREIGN PATENT DOCUMENTS

| | | |
|---|---|---|
| JP | 02-083022 | 3/1990 |
| JP | 02-090984 | 3/1990 |

OTHER PUBLICATIONS

Korean Office Action, issued in the corresponding Korean patent application No. 10-2018-7034399, dated Feb. 1, 2020, 9 pages (including machine translation); the cited references being previously filed in IDS.

Extended European Examination Report, issued in the corresponding European patent application No. 17792678.9, dated Nov. 29, 2019, 10 pages.

\* cited by examiner

[Figure 1]
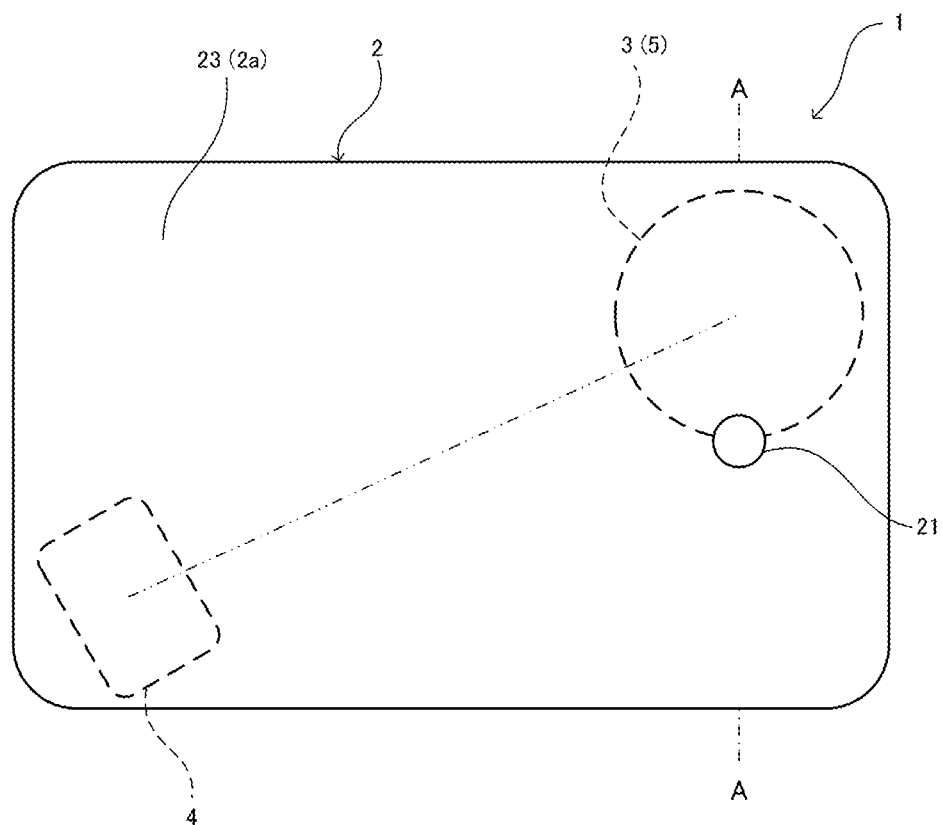

[Figure 2]
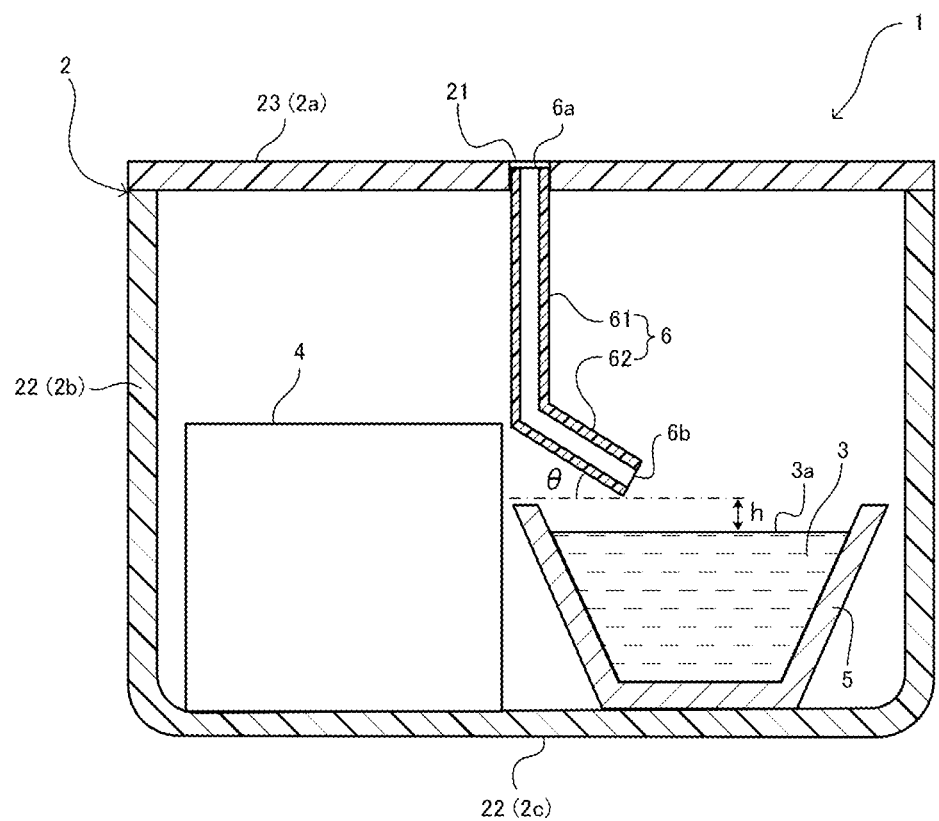

[Figure 3]
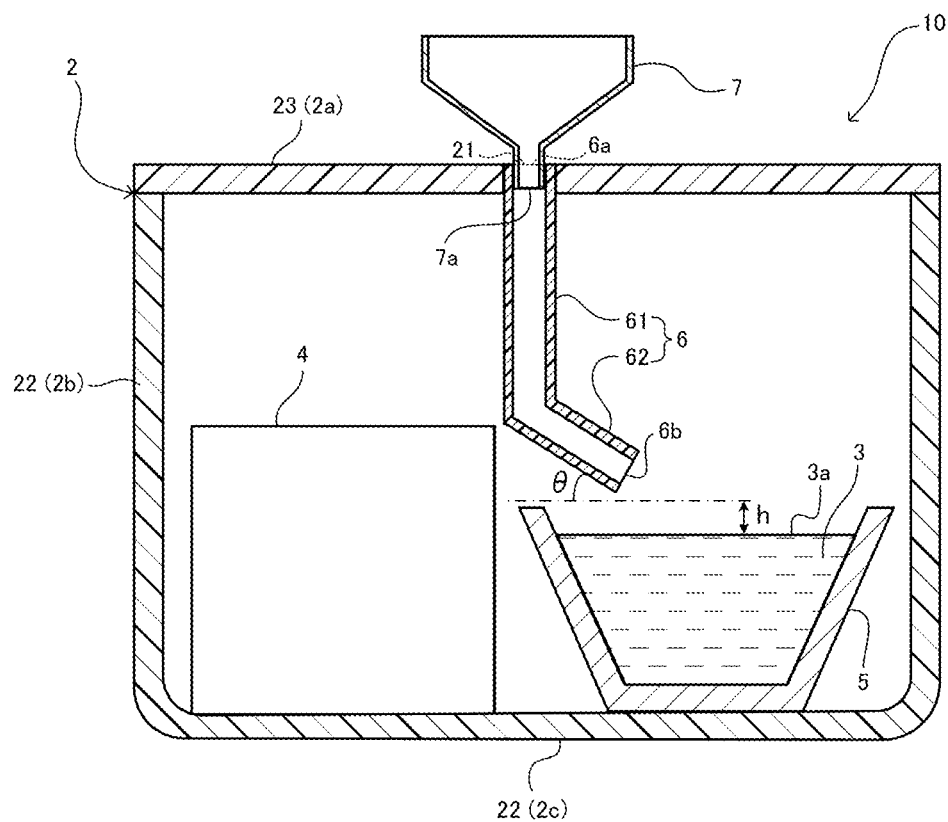

[Figure 4]
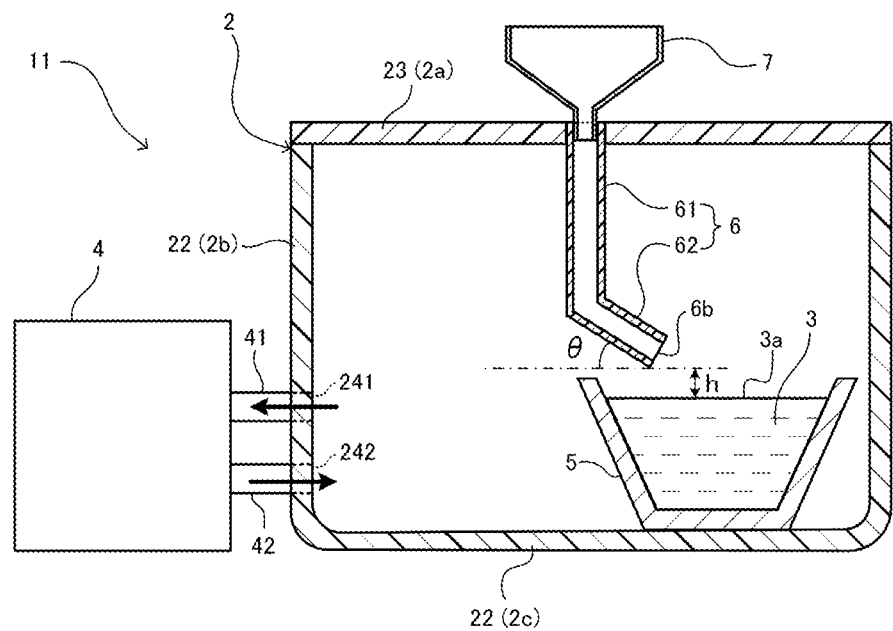

400 # POWDER DUSTINESS EVALUATION METHOD AND POWDER DUSTINESS EVALUATION DEVICE

TECHNICAL FIELD

The present invention relates to a method for evaluating a scattering property of a powder and an apparatus for evaluating a scattering property of a powder.

BACKGROUND ART

For example, in the dental industry, as a die material (so-called dental embedding material) for use in producing a metal (such as gold tooth and silver tooth) to be used for dental treatment, or as an auxiliary material in producing a tooth mold, an artificial tooth, and the like, gypsum-based powder products and phosphate-based powder products are used. These dental powder products are set by being mixed with a liquid such as water at the time of use (at the time of producing embedding material, tooth mold, artificial tooth, and the like). Dust is generated in handling a powder product (hereinafter, referred to as "scattering property of powder"), and therefore products that generate only a small amount of dust (so-called dust-free type) so that a working environment can be kept comfortable are preferred and a large number of such products are distributed.

It is not limited to the dental industry that a working environment becomes good if the generation amount of dust is small in handling a powder product. For example, powder products (hereinafter, also simply referred to as "powders") are also widely used in various industrial fields such as construction industry (such as building industry and civil engineering industry), various types of manufacturing industry (such as steel industry, chemical/petroleum products industry, transportation machinery industry, and food manufacturing industry). It is often desired that powders used in various industrial fields and powders produced in various industrial fields also have characteristics that dust does not scatter as much as possible.

As one example in the above-described dental industry, Patent Literature 1 discloses invention relating to a low-dust powder dental gypsum composition composed of a four-component formulation containing (a) hemihydrate gypsum, (b) an adjuster, (c) a predetermined humectant, and (d) a predetermined anionic surfactant.

On the other hand, as a method for measuring a scattering property of a powder, a method in which dust is generated by some sort of method, a powder (dust) is collected on a filter from air in which the dust is contained, and the collection amount of the dust is quantified, a method in which a dust concentration in air is obtained from the information on the laser diffraction of sample air, or the like has been conventionally adopted. For example, the aforementioned Patent Literature 1 describes in the examples thereof a method for measuring the mass concentration of dust in such a way that: a predetermined mass of a powder is taken in a metal cylindrical can to be shaken up and down 5 times at 1 up-and-down cycle per second; and the lid is detached immediately after the shaking to measure the mass concentration of dust released from the surface with a digital dust meter at 3 minutes after detaching the lid.

CITATION LIST

Patent Literature

Patent Literature 1: Japanese Patent Laid-Open No. 62-212255

SUMMARY OF INVENTION

Technical Problem

The present inventors have noticed that in conventional methods for measuring a scattering property of a powder, the difference in the measurement result is small between a powder product on which a treatment for suppressing the occurrence of dust has been applied (so-called dust-free product) and a powder product on which such a treatment has not been applied. A difference in the measurement result is still less hardly seen between dust-free powders, so that it has been difficult to evaluate the difference in performance through comparison between dust-free products. Therefore, even if a dust-free powder from which the generation amount of dust can be made smaller than the conventional dust-free powders is developed, there is a possibility that the excellent performance cannot be evaluated accurately, and the strong points and values of the product cannot be shown properly. Such a circumstance, if brought about, can be a hindrance to the sales of excellent products.

Thus, the present invention intends to provide a method by which a scattering property of a powder can be more clearly evaluated.

Solution to Problem

Conventionally, it has been considered that a large amount of dust is generated by shaking a powder as described in the aforementioned Patent Literature 1. However, the present inventors have conducted various studies to obtain a finding that a larger amount of dust is in fact generated at the moment of contact between a powder and a liquid when the powder is dropped onto the liquid, and thus the present invention has been completed.

That is, the present invention provides a method for evaluating a scattering property of a powder, the method including dropping a powder to be evaluated onto a liquid placed in a box, thereby scattering the powder as dust, and measuring a dust concentration in air in the box with a dust meter.

Advantageous Effects of Invention

The present invention can provide a method by which a scattering property of a powder can be more clearly evaluated.

BRIEF DESCRIPTION OF DRAWINGS

FIG. 1 is a diagram illustrating an outline configuration of an apparatus for evaluating a scattering property of a powder according to one embodiment of the present invention.

FIG. 2 is a schematic diagram of a section taken along line A-A in FIG. 1.

FIG. 3 is a section view illustrating an outline configuration of an apparatus for evaluating a scattering property of a powder according to another embodiment of the present invention, the section view corresponding to FIG. 2.

FIG. 4 is a section view illustrating an outline configuration of an apparatus for evaluating a scattering property of a powder according to yet another embodiment of the present invention, the section view corresponding to FIG. 2.

DESCRIPTION OF EMBODIMENTS

Hereinafter, embodiments of the present invention will be described, but the present invention is not limited to the following embodiments.

A method for evaluating a scattering property of a powder according to one embodiment of the present invention includes dropping a powder to be evaluated onto a liquid placed in a box, thereby scattering the powder as dust in the box, and measuring a dust concentration in air in the box with a dust meter.

When the powder to be evaluated drops onto the liquid placed in the box, a larger amount of dust can be generated in the box than in the case where the powder is dropped onto a place where the liquid does not exist. In this way, in the present invention, by actively scattering the powder to be evaluated as dust and measuring the dust concentration in air in the box on that occasion with a dust meter, whether the powder is easy to scatter or hard to scatter is evaluated. In other words, by dropping a powder onto a liquid placed in a box to scatter the powder actively as dust, the difference in the value of the concentration of the dust in air in the box becomes clearer between a powder that is easy to scatter and a powder that is hard to scatter. Therefore, the evaluation of the difference in performance between dust-free powders through comparison can also be conducted, so that the scattering property of a powder can be more clearly evaluated. That is, with respect to the evaluation of a scattering property for a powder or powders, the present method is more suitable for relatively evaluating the scattering property for a plurality of powders through comparison.

Hereinafter, the method for evaluating a scattering property of a powder according to one embodiment of the present invention will be described in detail with reference to the accompanying drawings usable for the method, each illustrating an outline configuration of an apparatus for evaluating a scattering property of a powder according to one embodiment of the present invention. Incidentally, the same reference sign is given to the components which are common in respective figures, and the description may be omitted.

FIG. 1 is a plan view viewed from above, the plan view schematically illustrating an outline configuration of arrangement relation in an apparatus 1 for evaluating a scattering property of a powder according to one embodiment of the present invention. FIG. 2 is a section view taken along line A-A in FIG. 1 and is a schematic diagram illustrating a state where a liquid 3 is arranged in a box 2. The apparatus 1 for evaluating a scattering property illustrated in FIG. 1 and FIG. 2 is provided with: the box 2 in which the liquid 3 is placed; and a dust meter 4 that measures the dust concentration in air in the box 2 when a powder to be evaluated drops onto the liquid 3 placed in the box to scatter as dust.

The box 2 can form a space (space to be an object of measurement) where the powder to be evaluated scatters as dust. The shape of the box 2 is not particularly limited and can be a shape having an upper portion 2a, a side portion 2b, and a bottom portion 2c, and when the shape is expressed in terms of a planar view shape viewed from the upper portion 2a or from the bottom portion 2c, examples thereof include an approximately triangular shape, an approximately square shape, an approximately polygonal shape, an approximately circular shape, and an approximately elliptical shape. For example, the box 2 in an approximately rectangular parallelepiped shape having the upper portion 2a, the side portion 2b, and the bottom portion 2c can be suitably used. It is preferable that the volume of the box 2, namely the volume of the space into which a powder is scattered, be about 10 to about 300 L, more preferably about 10 to about 150 L.

It is preferable that the box 2 be provided with a hole portion 21, to be an inlet of a powder into the box 2, at a position above the level 3a of the liquid 3 to be placed in the box 2 in order to drop the powder onto the liquid 3 placed in the box 2. More preferably, as illustrated in FIG. 1 and FIG. 2, the hole portion 21 is provided at the upper portion 2a of the box 2 in that the hole portion 21 is positioned above the level 3a of the liquid 3 to be placed in the box 2, thereby making it easy to drop the powder from the hole portion 21 onto the liquid 3 placed in the box 2. The use of a supply path, which will be described later, allows the powder to drop onto the liquid 3 placed in the box 2 even if the hole portion is provided at the side portion 2b of the box 2 as long as the position is above the level 3a of the liquid 3.

Although the use of the box 2 whose upper portion 2a is open allows the powder to drop from the opening onto the liquid 3 placed in the box 2, the box 2 provided with a hole portion 21 is preferable in that the portions other than the hole portion 21 can form a closed space (almost tightly closed space). Such an almost tightly closed box 2 can make it hard for dust, which is generated when the powder is dropped onto the liquid 3 placed in the box 2, to be subjected to an influence of an air stream outside the box 2. As a result, the measurement accuracy can be enhanced. Accordingly, from the viewpoint of capable of contributing to the enhancement of the measurement accuracy, it is preferable that the box 2 be the almost tightly closed box 2 in which the portions other than the hole portion 21 form a closed space. In addition, from the viewpoint of the enhancement of the measurement accuracy and from the viewpoint that the powder, which has dropped onto the liquid 3, can scatter sufficiently as dust, it is preferable that the diameter of the hole portion 21 be about 10 to about 100 mm.

As illustrated in FIG. 2, it is preferable that the box 2 be provided with: a box main body 22 whose upper portion is open; and a lid 23 that covers the upper portion of the box main body 22 and that the above-described hole portion 21 be provided at the lid 23. In this case, the box main body 22 constitutes the side portion 2b and the bottom portion 2c of the box 2, and the lid 23 constitutes the upper portion 2a of the box 2. The use of the box 2 provided with: a box main body 22; and a lid 23 having a hole portion 21 makes it easy to arrange the liquid 3 and the dust meter 4 in the box 2 and makes the measurement operation easy by detaching the lid 23 from the box main body 22 at a measurement preparation stage before the measurement. In addition, when the measurement is performed, putting the lid 23 on the upper portion of the box main body 22 allows the above-described almost tightly closed box to be formed, thereby capable of contributing to the enhancement of the measurement accuracy.

Although not illustrated in the figures, a slide type or push-pull type opening/closing portion may be provided at the upper portion 2a and/or the side portion 2b of the box 2 in place of the lid 23 or together with the lid 23. By making the opening/closing portion open, the liquid 3 and the dust meter 4 can be arranged in the box 2 at a measurement preparation stage, and the liquid 3 and the dust meter 4 can be taken out of the box 2 when the measurement is completed or when the measurement is not performed. In addition, when the measurement is performed, making the opening/closing portion close allows the above-described almost tightly closed box to be formed, thereby capable of contributing to the enhancement of the measurement accuracy.

It is preferable that the box 2 be transparent or semitransparent to such an extent that the inside of the box 2 is visually recognizable from the outside of the box 2. In this case, the whole or part of the box 2 may be transparent or semitransparent as long as the inside of the box 2 is visually recognizable from the outside of the box 2. Examples of the material for the box 2 whose inside is visually recognizable from outside include plastics and glass, and from the viewpoint of production costs, mass, handling properties, safety, etc., plastics are preferable. Examples of the plastics include polypropylene, polyethylene, acrylic resins, and polyester resins. In the case where the box is provided with the above-described box main body 22 and lid 23, or the above-described box main body 22 and opening/closing portion, the box main body 22 and the lid 23, or the box main body 22 and the opening/closing portion may be formed with the same type of material or may be formed with different types of materials.

The powder to be evaluated is not particularly limited. Any powder having a possibility of scattering as dust when used for applications according to the powder can be the object of evaluation. Examples of the material for the powder include cereal flour such as wheat flour, rice flour, corn flour, and dogtooth violet starch, inorganic powders such as calcium sulfate, calcium carbonate, calcium hydroxide, silicon dioxide, talc, iron oxide, aluminum, aluminum oxide, aluminum hydroxide, magnesium oxide, and magnesium hydroxide, and synthetic resin powders. In addition, for example, powder products obtained by mixing different types or the same types of a plurality of powders, such as gypsum, mortar, cement, and dental powder products, can also be used as the powder to be evaluated.

The method and the apparatus 1 according to the present embodiment are suitable for relatively evaluating the scattering property of a powder, as described previously, and therefore as a powder to be evaluated, a product on which a treatment of suppressing the occurrence of dust is applied, namely a powder product which is sold as a so-called dust-free product, is more suitable. Examples of more suitable powder products include dental powder products such as dental gypsum-based embedding materials, dental phosphate-based embedding materials, dental silica-based embedding materials, dental hard gypsum, dental superhard gypsum, and dental calcined gypsum.

It is preferable that the amount of a powder to be dropped onto the liquid 3 be 0.05 to 0.80 g, more preferably 0.08 to 0.65 g per 1 L of the volume of the box 2 so that an appropriate amount of the powder can scatter as dust in the box 2. The amount of the powder to be dropped onto the liquid 3 can be appropriately adjusted according to the characteristics of the powder to be evaluated, such as density.

The liquid 3 to be placed in the box 2 may be prepared in the box 2 at the time of measurement at the latest. When the powder drops onto the liquid 3 in measuring the dust concentration, the powder is mixed into the liquid 3, and therefore it is desirable that the liquid 3 be replaced every time the dust concentration of the powder is measured. Therefore, the liquid 3 may be placed in the box 2 preferably at the time of measurement, more preferably at every measurement. Still more preferably, as illustrated in FIG. 2, the liquid may be placed in the box 2 in such a way that the liquid is put in a container 5, the upper portion of which is open, at the time of measurement, and the container 5 with the liquid 3 being put therein is accommodated in the box 2. The use of such a container 5 makes it easy to replace the liquid 3 and to wash the part for putting the liquid 3 therein.

In the case where the above-described container 5 is used, the apparatus 1 for evaluating a scattering property can be further provided with a container 5 the upper portion of which is open and in which the liquid 3 is to be put (hereinafter, sometimes referred to as "container for liquid"). In this case, it is desirable that the container 5 for liquid be detached at every measurement, and therefore it is preferable that in the box 2, a mark be provided at a position where the container 5 for liquid is arranged, and it is also preferable that a fixing portion for fixing the container 5 for liquid at a predetermined position in the box 2 be provided. As the position where the liquid 3 (container 5 for liquid) is arranged in the box 2, an edge in the box 2 is preferable. For example, in the case where the box 2 has a shape containing corners (including round corners) in the planar view of the bottom portion 2c, such as the box 2 of an almost rectangular parallelepiped, as illustrated in FIG. 1, it is preferable that the liquid 3 (container 5 for liquid) be placed at a corner in the bottom portion 2c in the box 2. Separating the dust meter 4 at a certain distance from the liquid 3 that is a source of generating dust by arranging the liquid 3 at a position of an edge or a corner in the box 2 and arranging the dust meter 4, which will be described later, so as to oppose to the position of the liquid 3, or by other methods, can contribute to the enhancement of the measurement accuracy.

The container 5 for liquid is not particularly limited as long as it has a shape whose upper portion is open in such an extent that the powder to be evaluated drops onto the level 3a of the liquid 3 which is put in the container 5 to enable sufficient contact. Examples of such a container 5 include a dish type, a bowl type, and a cup type. It is preferable that the liquid 3 be put in the container 5 in such an amount that the liquid 3 has a certain extent of depth so that the powder which has dropped onto the liquid 3 can scatter sufficiently as dust, and therefore it is preferable that the container 5 be of a bowl type or of a cup type. The amount of the liquid 3 to be placed in the box 2 is not particularly limited and can be appropriately determined according to the volume of the box 2 and the use amount of the powder, and it is preferable that the amount of the liquid to be placed in the box 2 be set to 50 to 2400 mL, more preferably 80 to 1000 mL.

Incidentally, as described above, from the viewpoint of easiness of replacement of the liquid 3, and other viewpoints, it is preferable that the liquid 3 be put in the container 5 for liquid, which is other than the box 2, but the liquid 3 may be put directly in the box 2. For example, the liquid 3 may be placed in the box 2 by being put in a liquid injection portion formed in a dish shape, a bowl shape, a cup shape, and the like, the liquid injection portion provided in the box 2, or by being put in a liquid injection portion formed with a partition plate or the like.

The size of the opening of the container 5 for liquid or the liquid injection portion (size of level 3a) is not particularly limited as long as the size is in such an extent that the powder to be evaluated drops onto the level 3a of the liquid 3 to enable sufficient contact, and the powder, when drops onto the liquid 3, can sufficiently scatter as dust. It is preferable that the size of the opening of the container 5 for liquid or the liquid injection portion (size of level 3a) be larger than the diameter of the previously described hole portion 21 of the box 2 and the width or the diameter of the supply path, which will be described later, that introduces the powder from the hole portion 21 to the liquid 3.

It is preferable to use the type of liquid 3 according to the actual usage conditions of the powder to be evaluated. For example, in the case where the powder to be evaluated is a dental gypsum-based embedding material or calcined gypsum (such as dental hard gypsum, dental superhard gypsum and dental calcined gypsum) for dental models, the dental gypsum-based embedding material or the calcined gypsum for dental models is used by being mixed with water, and therefore it is preferable to use water as the liquid 3. In addition, for example, in the case where the powder to be evaluated is a phosphate-based dental embedding material, the dental embedding material is used by being mixed with an aqueous solution of colloidal silica, and therefore it is preferable to use an aqueous solution of colloidal silica as the liquid 3. Further, in the case where the application of the powder to be evaluated is not specified, in the case where a powder has diverse applications, in the case where the powder is not used by being kneaded with a liquid, or other cases, it is preferable to use water as the liquid 3.

To drop the powder onto the liquid 3 placed in the box 2, it is preferable to use a supply path 6 that introduces the powder from the hole portion 21 provided at the box 2 to the liquid 3 placed in the box 2. In the case where this supply path 6 is used, the apparatus 1 for evaluating a scattering property can be further provided with a supply path 6 that introduces the powder from the hole portion 21 to the liquid 3. Specifically, the supply path 6 can be provided so as to be connected to the aforementioned hole portion 21 provided at the box 2. In this case, the side of the hole portion 21 in the supply path 6 can be used as a portion where the powder is introduced (introduction portion) 6a, and the edge on the opposite side of the introduction portion 6a can be used as a portion where the powder is supplied to the liquid 3 (supply portion) 6b. In FIG. 2, the configuration in which the hole portion 21 and the supply path 6 are connected in such a way that the side of the introduction portion 6a in the supply path 6 is inserted and accommodated in the hole portion 21 of the box 2 is given as an example, but the supply path 6 may be provided so that the side of the introduction portion 6a penetrates from the hole portion 21 to the outside of the box 2.

The supply path 6 is provided so that the powder, when drops onto the liquid 3 placed in the box 2, can be scattered as dust. Examples of the shape of the supply path 6 include a tubular shape, a semi-tubular shape, and a slope shape, and examples of the shape of the section of the supply path 6 include a circular shape, elliptical shape, a square shape, a rectangular shape, an arch shape, and a U-shape It is preferable that the supply path 6 have a tubular shape (supply pipe) so that the powder, when drops onto the liquid 3, can scatter as dust without scattering as dust in the space in the box 2 at a stage in which the powder passes through the supply path 6 before the powder drops onto the liquid 3. The width (diameter) of the supply path 6 (supply pipe) and the width (diameter) of the above-described introduction portion 6a and supply portion 6b can be set so as to be about the same size as the diameter of the previously described hole portion 21 provided at the box 2.

The supply path 6 may be provided in a linear shape from the hole portion 21 of the box 2 toward the liquid 3, may be provided in a curved shape, or may be provided in a linear shape from the hole portion 21 toward the liquid 3 along the direction of the height of the box 2. Further, the supply path 6 may be provided with: a portion (perpendicular portion) 61 along the direction of the height of the box 2 (vertical direction relative to level 3a of liquid 3); and a portion (inclination portion) 62 inclined relative to the direction of the height of the box 2 or relative to the level 3a of the liquid 3. In this case, in the supply path 6, the side of the introduction portion 6a may be the inclination portion or the perpendicular portion, and the side of the supply portion 6b may also be the inclination portion or the perpendicular portion.

More preferably, as illustrated in FIG. 2, the supply path 6 is inclined, on a side of a supply portion 6b that supplies the powder to the liquid 3, relative to the level 3a of the liquid 3, and comprises an inclination portion 62 that slides the powder down toward the liquid 3. The powder supplied from the supply portion 6b that is provided continuously to this inclination portion 62 drops onto the liquid 3 from an oblique upper direction relative to the level 3a of the liquid 3. By allowing the supply path 6 to be provided with the inclination portion 62, the powder, when drops onto the liquid 3 from the inclination portion 62, can be actively scattered as dust. It is preferable that the inclination portion 62 have a configuration such that at least the side of the supply portion 6b is inclined relative to the level 3a of the liquid 3, and the whole of the supply path 6 may be inclined relative to the level 3a of the liquid 3.

It is preferable that the angle θ made by the inclination portion 62 and the level 3a of the liquid 3 be 20 to 70°, more preferably 30 to 60°. Due to the inclination portion 62 in such a range of angles, it becomes easier for the powder that has dropped onto the liquid 3 from the supply portion 6b at the tip of the inclination portion 62 to scatter as dust.

Incidentally, in FIG. 2, a tubular supply path (supply pipe) 6 is illustrated as an example. In the supply pipe 6, the side of the connection with the hole portion 21 of the box 2 is used as an introduction port (introduction portion) 6a to which a powder is introduced, and the opposite side of the introduction port 6a is used as a supply port (supply portion) 6b from which the powder is supplied to the liquid 3. The supply pipe 6 is provided with: the perpendicular portion 61 in which the side of the introduction port 6a is formed along the direction of the height of the box 2; and the inclination portion 62 formed continuously from the perpendicular portion 61 to the supply port 6b.

It is preferable that in the supply path 6, the supply portion 6b be provided at a predetermined height apart from the level 3a of the liquid 3 so that the powder that has dropped onto the liquid 3 can more easily scatter as dust. In the apparatus illustrated in FIG. 2, in the supply path 6, the supply port (supply portion) 6b is provided at a predetermined height h apart from the level 3a of the liquid 3. It is preferable that the distance (height) h between the level 3a of the liquid 3 and the lower end of the supply port (supply portion) 6b be 1 to 30 mm, more preferably 5 to 15 mm.

As illustrated in FIG. 3, it is preferable to use a hopper section 7 that is connected on the hole portion 21 of the box 2 so that the powder can be easily introduced in the box 2 and that the powder can be easily put in the introduction portion 6a in the supply path 6. In this case, an apparatus 10 for evaluating a scattering property can be provided with a hopper section 7 on the box 2, the hopper section 7 to be connected to the hole portion 21 of the box 2. FIG. 3 is an outline configuration diagram illustrating an example in which the hopper section 7 is attached to the hole portion 21 of the box 2 in the apparatus illustrated in FIG. 2. In the apparatus 10 illustrated in FIG. 3, an end portion 7a on the outlet side of the hopper section 7 is inserted in the introduction port 6a in the supply path 6 in which the side of the introduction port 6a is inserted and accommodated in the hole portion 21 of the box 2, but the connection mode of the hopper section 7, the hole portion 21, and the supply path 6 (introduction port 6a) is not limited. For example, the introduction port 6a in the supply path 6 may be provided so as to penetrate from the hole portion 21 to the outside of the box 2, and the end portion 7a on the outlet side of the hopper section 7 may be connected to the introduction port 6a at a position outside the box 2, the position apart upward from the hole portion 21 of the box 2. In addition, for example, the end portion 7a on the outlet side of the hopper section 7 may penetrate through the hole portion 21 to be connected to the introduction port 6a in the supply path 6 at a position inside the box 2, the position apart downward from the hole portion 21.

As the dust meter 4, a general-purpose dust measurement device for use in measuring working environments can be used. Examples of the dust meter 4 that can be used include a light scattering type dust measurement device, alight absorption type dust measurement device, and a volt balance type dust measurement device. Among these, a light scattering dust measurement device is preferable from the viewpoint of easy usability.

It is preferable that the dust meter 4 be placed in the box 2 at the time of use (at the time of measurement). Due to the dust meter 4 arranged in the box 2, the dust concentration in air in the box 2 when the powder is dropped onto the liquid 3 placed in the box 2 and is scattered as dust can be measured with good accuracy. As illustrated in FIG. 1, the dust meter 4 is more preferably arranged at a position of an edge (corner) in the box 2, and it is preferable to arrange the dust meter 4 so as to face to the previously described position of arranging the liquid 3 in that such arrangement expands the measurement range and can contribute to the enhancement of the measurement accuracy.

The dust meter 4 is not necessarily placed in the box 2 at the time of use (at the time of measurement) and may be placed outside the box 2 as long as the dust concentration in air in the box can be measured. For example, as illustrated in FIG. 4, an air inlet pipe 41 for sucking air in the box 2 and an exhaust pipe 42 for exhausting the sucked air out into the box 2 can be attached to the dust meter 4 in the apparatus 11 for evaluating a scattering property. By using the dust meter 4 provided with the air inlet pipe 41 and the exhaust pipe 42 each connected to the inside of the box 2, the dust concentration in air in the box 2 can be measured with the dust meter 4 even in the case where the dust meter 4 is placed outside the box 2. In this case, an air inlet hole 241 for feeding air in the box 2 into the dust meter 4 through the air inlet pipe 41 by being connected to the air inlet pipe 41, or an exhaust hole 242 for feeding air into the box 2 through the exhaust pipe 42 by being connected to the exhaust pipe 42 can be provided at the box 2. In the apparatus 11 for evaluating a scattering property illustrated in FIG. 4, the air inlet pipe 41 is connected to the air inlet port of the dust meter 4 and the air inlet hole 241 provided at the side portion 2b of the box 2, and the exhaust pipe 42 is connected to the exhaust port of the dust meter 4 and the exhaust hole 242 provided at the side portion 2b of the box 2.

The dust concentration to be measured with the dust meter 4 can be used for evaluating the scattering property of a powder. When the value of the dust concentration is high, the powder can be evaluated as easily scatters, and when the value of the dust concentration is low, the powder can be evaluated as hardly scatters. It is preferable to measure at least one of the number concentration [number/m$^3$] and the mass concentration [mg/m$^3$] of dust as the dust concentration. In addition, it is preferable to measure at least one of the maximum value and the integrated value of the dust concentration, more preferably both of them. Each of the maximum value and the integrated value of the dust concentration can be obtained by measuring the dust concentration at a predetermined time (for example, 1 minute) interval, thereby acquiring a plurality (for example, 5 points) of measured values.

It is preferable that the measurement procedure in the method for evaluating a scattering property of a powder according to the present embodiment include: a step of arranging the liquid 3 (more preferably, container 5 with liquid 3 being put therein) in the box 2; a step of starting the measurement with the dust meter 4; and a step of dropping the powder to be evaluated onto the liquid 3. This measurement procedure may include a step of installing the dust meter 4 in the box 2 or outside the box 2 before starting the measurement with the dust meter 4. More preferably, the measurement with the dust meter 4 is started before dropping the powder onto the liquid 3 to acquire a first measured value as a blank, and thereafter the powder is dropped onto the liquid 3. In addition, it is preferable to complete the measurement when the amount of dust is lowered to about the same extent as the first measured value (blank), and it is preferable to measure the dust concentration at a predetermined time interval (for example, interval of 10 seconds to 120 seconds) from the start of the measurement to the completion of the measurement.

Respective types of constitution described above can be arbitrarily combined. In addition, the method for evaluating a scattering property of a powder according to one embodiment of the present invention can also take the following constitution.

[1] A method for evaluating a scattering property of a powder, the method comprising dropping a powder to be evaluated onto a liquid placed in a box, thereby scattering the powder as dust in the box, and measuring a dust concentration in air in the box with a dust meter.

[2] The method for evaluating a scattering property of a powder according to [1], wherein the box comprises a hole portion, to be an inlet of the powder into the box, at a position above a level of the liquid to be placed in the box.

[3] The method for evaluating a scattering property of a powder according to [2], wherein the box comprises: a box main body whose upper portion is open; and a lid that covers the upper portion of the box main body, and the lid comprises the hole portion.

[4] The method for evaluating a scattering property of a powder according to [2] or [3], wherein the powder is dropped onto the liquid using a supply path that introduces the powder from the hole portion to the liquid.

[5] The method for evaluating a scattering property of a powder according to [4], wherein the supply path is inclined, on a side of a supply portion that supplies the powder to the liquid, relative to the level of the liquid, and comprises an inclination portion that slides the powder down toward the liquid.

[6] The method for evaluating a scattering property of a powder according to [5], wherein the supply portion in the supply path is provided at a predetermined height apart from the level of the liquid.

[7] The method for evaluating a scattering property of a powder according to any one of [1] to [6], wherein the liquid is put in a container whose upper portion is open, the container with the liquid being put therein is accommodated in the box, and the liquid is thereby placed in the box.

[8] The method for evaluating a scattering property of a powder according to any one of [1] to [7], wherein the powder is a dental powder product.

Further, the apparatus for evaluating a scattering property of a powder according to one embodiment of the present invention can also take the following constitution.

[9] An apparatus for evaluating a scattering property of a powder, the apparatus comprising: a box in which a liquid is to be placed; and a dust meter that measures a dust concentration in air in the box when a powder to be evaluated drops onto a liquid placed in the box and scatters as dust.

[10] The apparatus for evaluating a scattering property of a powder according to [9], wherein the box comprises a hole portion, to be an inlet of the powder into the box, at a position above a level of the liquid to be placed in the box.

[11] The apparatus for evaluating a scattering property of a powder according to [10], wherein the box comprises: a box main body whose upper portion is open; and a lid that covers the upper portion of the box main body, and the lid comprises the hole portion.

[12] The apparatus for evaluating a scattering property of a powder according to [10] or [11], further comprising a supply path that introduces the powder from the hole portion to the liquid.

[13] The apparatus for evaluating a scattering property of a powder according to [12], wherein the supply path is inclined, on a side of a supply portion that supplies the powder to the liquid, relative to the level of the liquid, and comprises an inclination portion that slides the powder down toward the liquid.

[14] The apparatus for evaluating a scattering property of a powder according to [13], wherein the supply portion in the supply path is provided at a predetermined height apart from the level of the liquid.

[15] The apparatus for evaluating a scattering property of a powder according to any one of [9] to [14], further comprising a container whose upper portion is open, wherein the container is to be accommodated in the box, and the liquid is to be put in the container.

[16] The apparatus for evaluating a scatting property of a powder according to any one of [9] to [15], wherein the powder is a dental powder product.

EXAMPLES

Hereinafter, the present invention will be described more specifically giving Examples, but the present invention is not limited to the following Examples.

<Preparation of Apparatus>

A polypropylene storage case (trade name "ST BOX 25" manufactured by Astage CO., LTD.) of 360 mm in width, 240 mm in height, and 240 mm in depth (volume of about 20 L), the storage case provided with a box main body and a lid, was used as a box. In the lid of this box, a hole portion in a circular shape having a diameter of 30 mm was provided at a portion on the right-hand side portion in the width direction and on the approximately central portion in the depth direction (refer to FIG. 1). On one corner side in this box, a container whose upper portion is open was arranged, and a laser light scattering type dust meter (trade name "Dust Monitor Dust Meter DC170" manufactured by SATO-TECH) was arranged on the corner side diagonal to the corner where this container was arranged (refer to FIG. 1). The center-to-center distance between the container and the dust meter in planar view was about 200 mm. To drop a powder, a supply pipe that introduces the powder from the hole portion of the box into the container arranged in the box was used. In the box, a powder introduction port of the supply pipe (diameter of pipe: 30 mm, length of perpendicular portion: 60 mm, length of inclination portion: 95 mm, angle θ: 35°) was inserted into the hole portion of the box to connect the hole portion and the supply pipe (refer to FIG. 2 and FIG. 3).

Example 1

In Example 1, a dental gypsum-based embedding material (trade name "SaKura Quick 20" manufactured by Yoshino Gypsum Co., Ltd.) was used as a powder to be evaluated. This powder is used by being mixed with water, and therefore, 150 mL of water was put in advance in the container arranged in the box. On that occasion, the distance h between the level of the liquid in the container and the lower end of the supply port of the supply pipe was 5 mm. The measurement of the dust concentration with the dust meter was started before dropping the powder onto water. The interval of measuring the dust concentration was set to 1 minute, and at 10 seconds after the first measurement was completed, 5 g of the powder was dropped onto water in the container from a hopper section (refer to FIG. 3) attached to the hole portion of the box through the supply pipe, thereby scattering the powder as dust. Up to 5 measured values of the dust concentration (number concentration of particles having particle diameter of 0.5 μm or more) in air in the box on that occasion were acquired.

Example 2

In Example 2, the dust concentration was measured in the same manner as in Example 1 except that a powder obtained by adding a nonionic surfactant, as a treatment for suppressing the occurrence of dust, to the powder used in Example 1 (dental gypsum-based embedding material treated so as to be dust-free) was used in place of the powder used in Example 1.

Comparative Example 1

In Comparative Example 1, the dust concentration was measured in the same manner as in Example 1 except that water was not put in the container arranged in the box.

Comparative Example 2

In Comparative Example 2, the dust concentration was measured in the same manner as in Example 2 except that water was not put in the container arranged in the box.

Example 3

In Example 3, the dust concentration was measured in the same manner as in Example 1 except that white cement ("White Portland Cement" manufactured by TAIHEIYO CEMENT CORPORATION) was used as a powder to be evaluated in place of the powder used in Example 1.

Example 4

In Example 4, the dust concentration was measured in the same manner as in Example 3 except that a powder obtained by adding a nonionic surfactant, as a treatment for suppressing the occurrence of dust, to the powder used in Example 3 (white cement treated so as to be dust-free) was used in place of the powder used in Example 3.

Comparative Example 3

In Comparative Example 3, the dust concentration was measured in the same manner as in Example 3 except that water was not put in the container arranged in the box.

Comparative Example 4

In Comparative Example 4, the dust concentration was measured in the same manner as in Example 4 except that water was not put in the container arranged in the box.

Example 5

In Example 5, the dust concentration was measured in the same manner as in Example 1 except that dental hard gypsum (trade name "New Hi-Stone Yellow" manufactured by Yoshino Gypsum Co., Ltd.) was used as a powder to be evaluated in place of the powder used in Example 1 and that the amount of the powder dropped was changed from "5 g" in Example 1 to "10 g".

Example 6

In Example 6, the dust concentration was measured in the same manner as in Example 5 except that a powder obtained by adding a nonionic surfactant, as a treatment for suppressing the occurrence of dust, to the powder used in Example 5 (dental hard gypsum treated so as to be dust-free) was used in place of the powder used in Example 5.

Comparative Example 5

In Comparative Example 5, the dust concentration was measured in the same manner as in Example 5 except that water was not put in the container arranged in the box.

Comparative Example 6

In Comparative Example 6, the dust concentration was measured in the same manner as in Example 6 except that water was not put in the container arranged in the box.

The maximum value among the five measured values of the dust concentration measured in each of Examples and Comparative Examples, and the integrated value of the 5 measured values in total were used for evaluation. The results are shown in Tables 1 to 3.

TABLE 1

Results of experiments using dental gypsum-based embedding material

|  | Example 1 | Example 2 | Comparative Example 1 | Comparative Example 2 |
|---|---|---|---|---|
| Treated or not so as to be dust-free | Not treated | Treated | Not treated | Treated |
| Maximum value of dust concentration ($\times 10^4$ number/L) | 619 | 76 | 23 | 11 |
| Integrated value of dust concentration ($\times 10^4$ number/L) | 2246 | 158 | 44 | 26 |

TABLE 2

Results of experiments using white cement

|  | Example 3 | Example 4 | Comparative Example 3 | Comparative Example 4 |
|---|---|---|---|---|
| Treated or not so as to be dust-free | Not treated | Treated | Not treated | Treated |
| Maximum value of dust concentration ($\times 10^4$ number/L) | 315 | 68 | 159 | 40 |
| Integrated value of dust concentration ($\times 10^4$ number/L) | 1020 | 105 | 306 | 80 |

TABLE 3

Results of experiments using dental hard gypsum

|  | Example 5 | Example 6 | Comparative Example 5 | Comparative Example 6 |
|---|---|---|---|---|
| Treated or not so as to be dust-free | Not treated | Treated | Not treated | Treated |
| Maximum value of dust concentration ($\times 10^4$ number/L) | 209 | 60 | 55 | 29 |
| Integrated value of dust concentration ($\times 10^4$ number/L) | 600 | 80 | 118 | 46 |

From the comparison of the results of Examples 1 and 2 with the results of Comparative Examples 1 and 2, the comparison of the results of Examples 3 and 4 with the results of Comparative Examples 3 and 4, and the comparison of the results of Examples 5 and 6 with the results of Comparative Examples 5 and 6, it was found that the difference in the measured value of the dust concentration due to whether the powder was treated so as to be dust-free or not was larger in Examples than in Comparative Examples. Accordingly, it was ascertained that by dropping a powder onto a liquid placed in a box to scatter the powder actively as dust, the difference in the dust concentration in air in the box becomes clearer, so that the scattering property of a powder can be evaluated more clearly.

INDUSTRIAL APPLICABILITY

The method for evaluating a scattering property of a powder or the apparatus for evaluating a scattering property of a powder according to one embodiment of the present invention can evaluate the scattering property of a powder more clearly and therefore are useful in using, producing, selling, etc. a powder product, particularly in selling, etc. a powder product from which the generation amount of dust is suppressed.

REFERENCE SIGNS LIST 1, 10, 11 Apparatus for evaluating a scattering property of a powder
2 Box
3 Liquid
4 Dust meter
5 Container
6 Supply path

The invention claimed is:
1. A method for evaluating a scattering property of a powder, the method comprising:

dropping the powder to be evaluated onto liquid placed in a box, thereby scattering the powder as dust in the box; and measuring a concentration of the dust in air in the box with a dust meter wherein the box comprises:
a hole portion, as an inlet through the powder is introduced into the box; and a supply path,
the hole portion is positioned at a level higher than a surface of the liquid in the box,
the powder is dropped onto the liquid using the supply path that introduces the powder from the hole portion to the liquid,
the supply path comprises:
an introduction portion as an inlet of the supply path, from which the powder is introduced to the supply path;
a supply portion as an outlet of the supply path, from which the powder slides down toward the liquid; and
an inclination portion at a side of the supply portion in the supply path, and the supply path is inclined at the inclination portion, relative to the surface of the liquid.

2. The method for evaluating a scattering property of a powder according to claim 1,
wherein the box further comprises:
a box main body whose upper portion is open; and
a lid that covers the upper portion of the box main body, and the lid comprises the hole portion.

3. The method for evaluating a scattering property of a powder according to claim 1,
wherein the supply portion in the supply path is provided at a height apart from the surface of the liquid in a range from 1 mm to 30 mm.

4. The method for evaluating a scattering property of a powder according to claim 1,
wherein the liquid is introduced into a container whose upper portion is open,
the container including the liquid therein is accommodated in the box, and
the liquid is thereby placed in the box.

5. The method for evaluating a scattering property of a powder according to claim 1, wherein the powder is a dental powder product.

6. The method for evaluating a scattering property of a powder according to claim 1,
wherein the supply portion in the supply path is provided at a height apart from the surface of the liquid in a range from 5 mm to 15 mm.

7. The method for evaluating a scattering property of a powder according to claim 1,
wherein an angle between the inclination portion of the supply path and the surface of the liquid is in a range from 20° to 70°.

8. The method for evaluating a scattering property of a powder according to claim 1,
wherein the hole portion of the box and the introduction portion of the supply path are same.

9. An apparatus for evaluating a scattering property of a powder, the apparatus comprising:
a box in which liquid is to be placed; and
a dust meter that measures a concentration of the powder as dust in air in the box when the powder to be evaluated drops onto the liquid placed in the box and scatters as dust in the box,
wherein the box comprises:
a hole portion that is configured to be an inlet through which the powder is introduced into the box; and
a supply path that is configured to introduce the powder from the hole portion to the liquid,
the hole portion is configured to be placed at a level higher than a level of a surface of the liquid to be placed in the box,
the supply path comprises:
an introduction portion as an inlet of the supply path, from which the powder is introduced to the supply path;
a supply portion as an outlet of the supply path, from which the powder slides down toward the liquid; and
an inclination portion at a side of the supply portion in the supply path, and the supply path is inclined at the inclination portion, relative to the surface of the liquid.

10. The apparatus for evaluating a scattering property of a powder according to claim 9,
wherein the box further comprises:
a box main body whose upper portion is open; and
a lid that covers the upper portion of the box main body, and
the lid comprises the hole portion.

11. The apparatus for evaluating a scattering property of a powder according to claim 9,
wherein the supply portion in the supply path is provided at a height apart from the surface of the liquid in a range from 1mm to 30 mm.

12. The apparatus for evaluating a scattering property of a powder according to claim 9, further comprising a container in the box,
wherein the container is configured to accommodate the liquid therein, and
the liquid is to be introduced into the container from an upper portion thereof, the upper portion of the container being open.

13. The apparatus for evaluating a scattering property of a powder according to claim 9, wherein the powder is a dental powder product.

14. The apparatus for evaluating a scattering property of a powder according to claim 9,
wherein the supply portion in the supply path is provided at a height apart from the surface of the liquid in a range from 5 mm to 15 mm.

15. The apparatus for evaluating a scattering property of a powder according to claim 9,
wherein an angle between the inclination portion of the supply path and the surface of the liquid is in a range from 20° to 70°.

16. The apparatus for evaluating a scattering property of a powder according to claim 9,
wherein the hole portion of the box and the introduction portion of the supply path are same.

* * * * *